(12) United States Patent
Fuimaono et al.

(10) Patent No.: US 6,970,730 B2
(45) Date of Patent: *Nov. 29, 2005

(54) BASKET CATHETER WITH MULTIPLE LOCATION SENSORS

(75) Inventors: Kristine B. Fuimaono, Covina, CA (US); Maria G. Rangel, West Covina, CA (US); Dipen Shah, Geneva (CH)

(73) Assignee: Biosense Webster, Inc., Diamond Bar, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/839,036

(22) Filed: May 5, 2004

(65) Prior Publication Data

US 2004/0210121 A1 Oct. 21, 2004

Related U.S. Application Data

(63) Continuation of application No. 10/017,029, filed on Dec. 14, 2001, now Pat. No. 6,748,255.

(51) Int. Cl.[7] .............................................. A61B 5/042
(52) U.S. Cl. ...................... 600/374; 600/509; 607/122; 128/899
(58) Field of Search ............................... 600/374, 509; 607/122; 128/899

(56) References Cited

U.S. PATENT DOCUMENTS

| | | | |
|---|---|---|---|
| 5,255,679 A | 10/1993 | Imran | |
| 5,345,936 A | 9/1994 | Pomeranz et al. | |
| 5,411,025 A | 5/1995 | Webster, Jr. | |
| 5,628,313 A | 5/1997 | Webster, Jr. | |
| 5,772,590 A | 6/1998 | Webster, Jr. | |
| 5,782,239 A | 7/1998 | Webster, Jr. | |
| 6,292,695 B1 | 9/2001 | Webster, Jr. et al. | |
| 6,400,981 B1 | 6/2002 | Govari | |
| 6,584,345 B2 | 6/2003 | Govari | |
| 6,748,255 B2 * | 6/2004 | Fuimaono et al. .......... 600/374 |
| 2003/0093067 A1 | 5/2003 | Panescu | |
| 2003/0114846 A1 | 6/2003 | Fuimaono et al. | |

FOREIGN PATENT DOCUMENTS

| | | |
|---|---|---|
| EP | 0 835 634 A1 | 4/1998 |
| EP | 1 125 549 A2 | 8/2001 |
| EP | 1 323 451 A2 | 7/2003 |
| WO | WO 97/24983 | 7/1997 |
| WO | WO 98/29033 | 7/1998 |
| WO | WO 00/51683 | 9/2000 |

\* cited by examiner

Primary Examiner—Lee S. Cohen
(74) Attorney, Agent, or Firm—Christie, Parker & Hale, LLP

(57) ABSTRACT

An improved basket catheter is provided that is particularly useful for mapping the heart. The catheter comprises an elongated catheter body having proximal and distal ends and at least one lumen therethrough. A basket-shaped electrode assembly is mounted at the distal end of the catheter body. The basket assembly has proximal and distal ends and comprises a plurality of spines connected at their proximal and distal ends. Each spine comprises at least one electrode. The basket assembly has an expanded arrangement wherein the spines bow radially outwardly and a collapsed arrangement wherein the spines are arranged generally along the axis of the catheter body. The catheter further comprises a distal location sensor mounted at or near the distal end of the basket-shaped electrode assembly and a proximal location sensor mounted at or near the proximal end of the basket-shaped electrode assembly. In use, the coordinates of the distal location sensor relative to those of the proximal sensor can be determined and taken together with known information pertaining to the curvature of the spines of the basket-shaped mapping assembly to find the positions of the at least one electrode of each spine.

31 Claims, 6 Drawing Sheets

BASKET CATHETER WITH MULTIPLE LOCATION SENSORS

CROSS-REFERENCE TO RELATED APPLICATION

This application is a continuation of U.S. application Ser. No. 10/017,029, filed Dec. 14, 2001 now U.S. Pat. No. 6,748,255 the entire disclosure of which is incorporated herein by reference.

BACKGROUND OF THE INVENTION

The invention is directed to a catheter having a basket-shaped electrode array with two or more location sensors to provide improved mapping capabilities.

Electrophysiology catheters are commonly-used for mapping electrical activity in the heart. Various electrode designs are known for different purposes. In particular, catheters having basket-shaped electrode arrays are known and described, for example, in U.S. Pat. No. 5,772,590, the disclosure of which is incorporated herein by reference.

Additionally, it is generally known to incorporate into certain electrophysiology catheters a location or position sensor for determining the location of electrodes being used to map electrical activity. Such catheters are generally inserted percutaneously and fed through one or more major blood vessels into a chamber of the heart. A location sensor in the catheter, typically near the catheter's distal end, gives rise to signals that are used to determine the position of the device relative to a frame of reference that is fixed either externally to the body or to the heart itself. The location sensor may be active or passive and may operate by generating or receiving electrical, magnetic or ultrasonic energy fields or other suitable forms of energy known in the art.

U.S. Pat. No. 5,391,199, the disclosure of which is incorporated herein by reference, describes a position-responsive catheter comprising a miniature sensor coil contained in the catheter's distal end. The coil generates electrical signals in response to externally-applied magnetic fields, which are produced by field-generator coils placed outside the patient's body. The electrical signals are analyzed to determine three-dimensional coordinates of the coil.

International Publication No. WO 96/05768, the disclosure of which is also incorporated herein by reference, describes a position-responsive catheter comprising a plurality of miniature, preferably non-concentric sensor coils fixed in its distal end. As in U.S. Pat. No. 5,391,1999, electrical signals generated by these coils in response to an externally-applied magnetic field are analyzed so as to determine, for example, six-dimensional position and orientation coordinates of these coils.

Multiple position-sensing devices may be placed in a known, mutually-fixed spatial relation at or adjacent to the distal end of a catheter, as described, for example, in International Publication No. WO 97/24983, the disclosure of which is incorporated herein by reference. This publication describes a catheter having a substantially rigid structure at its distal end, to which one or more position sensors are fixed. The sensors are used to determine the position and orientation of the rigid structure.

SUMMARY OF THE INVENTION

The present invention is directed to an improved catheter having a basket-shaped electrode assembly. The basket-shaped electrode assembly can expand into a variety of positions and has two or more location sensors for determining the location of electrodes mounted on the assembly.

In one embodiment, the invention is directed to a catheter comprising an elongated catheter body having proximal and distal ends and at least one lumen therethrough. A basket-shaped electrode assembly is mounted at the distal end of the catheter body. The basket assembly has proximal and distal ends and comprises a plurality of spines connected, directly or indirectly, at their proximal and distal ends. Each spine comprises at least one electrode. The basket assembly has an expanded arrangement wherein the spines bow radially outwardly and a collapsed arrangement wherein the spines are arranged generally along the axis of the catheter body. The catheter further comprises a distal location sensor mounted at or near the distal end of the basket-shaped electrode assembly and a proximal location sensor mounted at or near the proximal end of the basket-shaped electrode assembly. In use, the coordinates of the distal location sensor relative to those of the proximal sensor can be determined and taken together with known information pertaining to the curvature of the spines of the basket-shaped mapping assembly to find the positions of the at least one electrode of each spine.

DESCRIPTION OF THE DRAWINGS

These and other features and advantages of the present invention will be better understood by reference to the following detailed description when considered in conjunction with the accompanying drawings wherein.

DETAILED DESCRIPTION OF THE INVENTION

Figure 1:
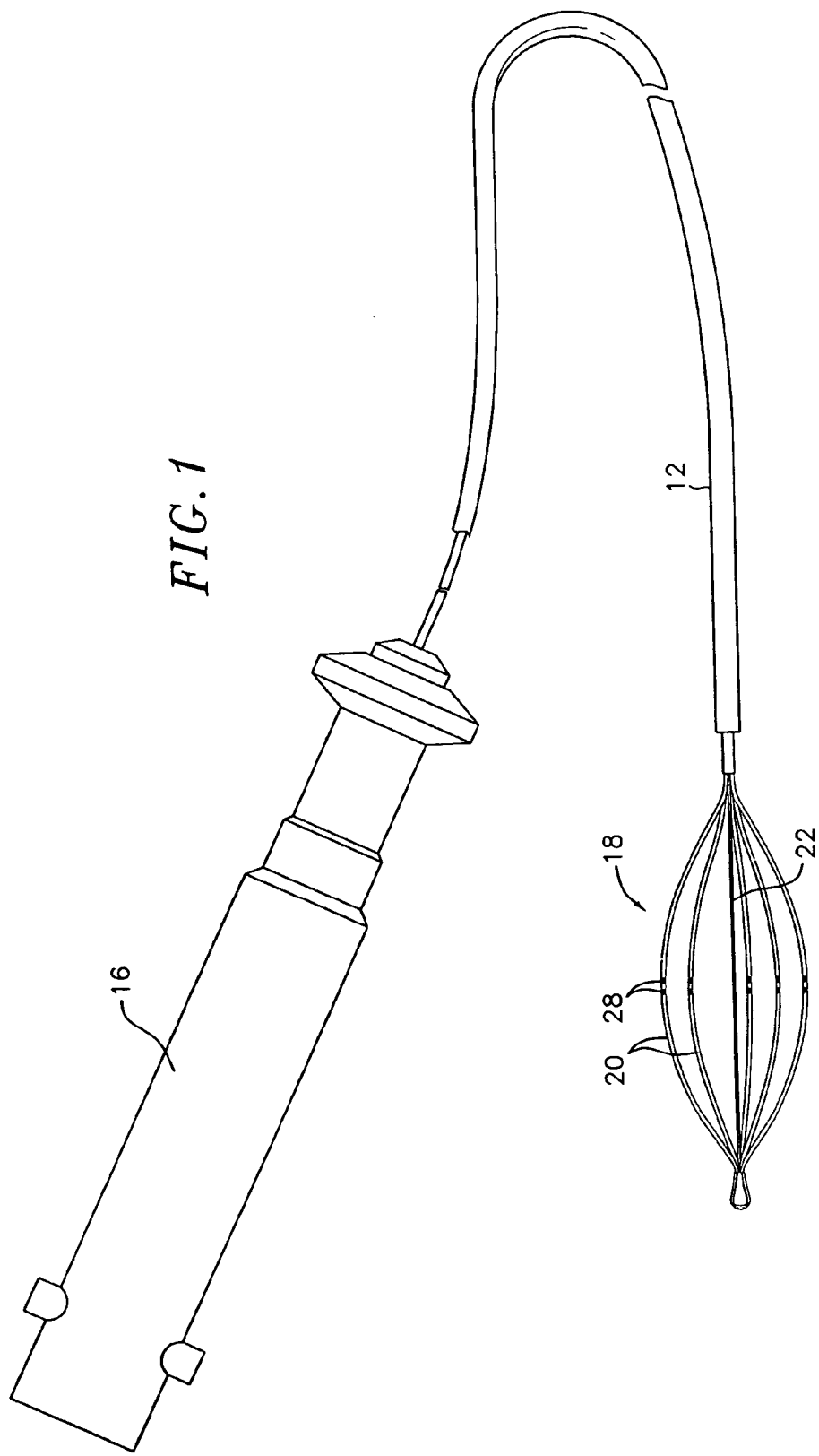
FIG. 1 is a perspective view of a catheter according to the invention.

The invention is directed to a catheter having a basket-shaped electrode array with two or more location sensors mounted at its distal end. As shown in FIG. 1, the catheter comprises an elongated catheter body 12 having proximal and distal ends, a control handle 16 at the proximal end of the catheter body, and a basket-shaped electrode assembly 18 mounted at the distal end of the catheter body 12.

The catheter body 12 comprises an elongated tubular construction having a single, axial or central lumen (not shown), but can optionally have multiple lumens if desired. The catheter body 12 is flexible, i.e., bendable, but substantially non-compressible along its length. The catheter body 12 can be of any suitable construction and made of any suitable material. A presently preferred construction comprises an outer wall made of polyurethane or PEBAX.RTM. (polyether block amide). The outer wall comprises an imbedded braided mesh of stainless steel or the like to increase torsional stiffness of the catheter body 12 so that, when the control handle 16 is rotated, the distal end of the catheter body will rotate in a corresponding manner.

The outer diameter of the catheter body 12 is not critical, but is preferably no more than about 8 french, more preferably 7 french. Likewise the thickness of the outer wall is not critical, but is preferably thin enough so that the central lumen can accommodate a puller wire, lead wires, sensor cables and any other wires, cables or tubes. If desired, the inner surface of the outer wall is lined with a stiffening tube (not shown) to provide improved torsional stability. An example of a catheter body construction suitable for use in connection with the present invention is described and depicted in U.S. Pat. No. 6,064,905, the entire disclosure of which is incorporated herein by reference.

Figure 2:
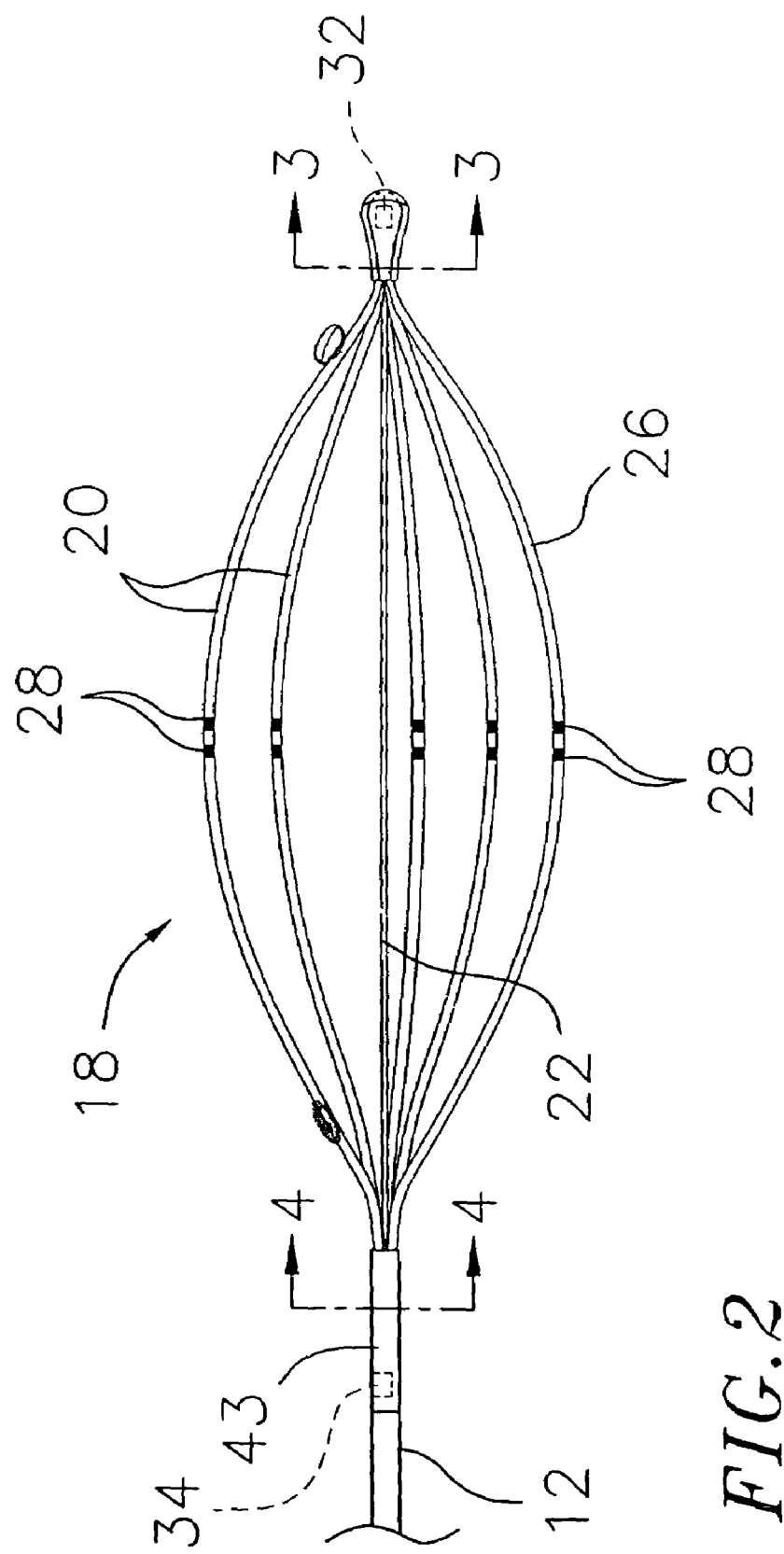
FIG. 2 is a close-up perspective view of the basket-shaped electrode assembly, the housing, and the distal end of the catheter body of the catheter shown in FIG. 1.

The basket-shaped electrode assembly 18 is mounted to the distal end of the catheter body 12. As shown in FIG. 2, the basket-shaped electrode assembly 18 comprises five spines 20 or arms mounted, preferably generally evenly-spaced, around an expander 22 so that the expander forms the axis of the electrode assembly. The spines 20 are all attached, directly or indirectly, to the expander 22 at their distal ends, and to the catheter body 12 at their proximal ends. As described in more detail below, the expander is moved longitudinally to expand and contract the electrode assembly, so that, in the expanded position the spines 20 are bowed outwardly and in the contracted position the spines are generally straight. As will be recognized by one skilled in the art, the number of spines 20 can vary as desired depending on the particular application, so that the assembly has at least two spines, preferably at least three spines, and as many as eight or more spines. As used herein, the term "basket-shaped" in describing the electrode assembly 18 is not limited to the depicted configuration, but can include other designs, such as spherical or egg-shaped designs, that include a plurality of expandable arms connected, directly or indirectly, at their proximal and distal ends.

Each spine 20 comprises a flexible wire 24 with a non-conductive covering 26 on which one or more ring electrodes 28 are mounted. In a preferred embodiment, the flexible wires 24 each comprise a flat Nitinol wire and the non-conductive coverings 26 each comprise a biocompatible plastic tubing, such as polyurethane or polyimide tubing. Alternatively, the spines 20 can be designed without the internal flexible wire 24 if a sufficiently rigid nonconductive material is used for the non-conductive covering 26 to permit expansion of the electrode assembly 18, so long as the spine has an outer surface that is non-conductive over at least a part of its surface for mounting of the ring electrodes 28.

Each of the ring electrodes 28 on the spines 20 is electrically connected to an appropriate mapping or monitoring system and/or source of ablation energy by means of an electrode lead wire 29. Each electrode lead wire 29 extends through the control handle 16, through a lumen in the catheter body, and into the non-conductive covering 26 of the corresponding spine 20. Each lead wire 29 is attached to its corresponding ring electrode 28 by any suitable method.

A preferred method for attaching a lead wire 29 to a ring electrode 28 involves first making a small hole through the wall of the non-conductive covering 26. Such a hole can be created, for example, by inserting a needle through the non-conductive covering 26 and heating the needle sufficiently to form a permanent hole. The lead wire 29 is then drawn through the hole by using a microhook or the like. The end of the lead wire 29 is then stripped of any coating and welded to the underside of the ring electrode 28, which is then slid into position over the hole and fixed in place with polyurethane glue or the like. Alternatively, each ring electrode 28 is formed by wrapping a lead wire 29 around the non-conductive covering 26 a number of times and stripping the lead wire of its own insulated coating on its outwardly facing surfaces.

As shown in the depicted embodiment, the expander 22 is generally coaxial with the catheter body 12. The expander 22 has a distal end at the distal end of the electrode assembly 18 and a proximal end extending out the distal end of the catheter body 12 and attached to the control handle 16, as will be described further below, so that the expander can be moved longitudinally relative to the catheter body 12 to thereby expand and contract the electrode assembly. The expander 22 comprises a material sufficiently rigid to achieve this function. In a preferred embodiment, the expander 22 comprises braided polyimide tubing, i.e., tubing having inner and outer layers of polyimide with a braided stainless steel mesh therebetween, as is generally known in the art. The expander has a guidewire lumen 30 that extends along its entire length. As will be described further below, the guidewire lumen 30 permits a guidewire to extend through the entire length of the catheter for introduction of the catheter into the body.

Alternatively, manipulation of the electrode assembly 18 can be achieved using a puller wire (not shown) that extends through the catheter body 12 and is fixed at its distal end to the distal end of the mapping assembly and at its proximal end to the control handle 16. Such a puller wire arrangement is disclosed, for example, in U.S. Pat. No. 5,772,590, the disclosure of which is incorporated herein by reference. Any other means for expanding and contracting the electrode assembly 18 can also be used in accordance with the invention. Alternatively, the basket-shaped mapping assembly 18 may be expanded and contracted by moving a guiding sheath proximally off the basket and distally over the basket, respectively, so that the catheter itself does not need to include a means for expanding and contracting the basket.

The catheter further includes two location sensors 32 and 34 for providing location information about each of the ring electrodes on the electrode assembly 18. The distal location sensor 32 is mounted at or near the distal end of the electrode assembly 18, and the proximal location sensor 34 is mounted at or near the proximal end of the electrode assembly, either on the assembly or on the catheter body, as described further below.

Each location sensor 32 and 34 is connected to a corresponding sensor cable 36 that extends through the catheter body 12 and control handle 16 and out the proximal end of the control handle within an umbilical cord (not shown) to a sensor control module (not shown) that houses a circuit board (not shown). Alternatively, the circuit board can be housed within the control handle 16, for example, as described in U.S. Pat. No. 6,024,739, the disclosure of which is incorporated herein by reference. The sensor cable 36 comprises multiple wires encased within a plastic covered sheath. In the sensor control module, the wires of the sensor cable are connected to the circuit board. The circuit board amplifies the signal received from the corresponding location sensor and transmits it to a computer in a form understandable by the computer by means of the sensor connector at the proximal end of the sensor control module. Also, because the catheter is designed for single use only, the circuit board preferably contains an EPROM chip that shuts down the circuit board approximately twenty-four hours after the catheter has been used. This prevents the catheter, or at least the location sensor, from being used twice.

Preferably each location sensor 32 and 34 comprises a magnetic-field-responsive coil, as described in U.S. Pat. No. 5,391,199, or more preferably, a plurality of such coils, as described in International Publication WO 96/05758. The plurality of coils enables six-dimensional position and orientation coordinates to be determined. Alternatively, any suitable position sensor known in the art may be used, such as electrical, magnetic or acoustic sensors. Suitable location sensors for use with the present invention are also described, for example, in U.S. Pat. Nos. 5,558,091, 5,443,489, 5,480, 422, 5,546,951, and 5,568,809, and International Publication Nos. WO 95/02995, WO 97/24983, and WO 98/29033, the disclosures of which are incorporated herein by reference. A preferred electromagnetic mapping sensor has a length of from about 3 mm to about 7 mm, preferably about 4 mm.

Alternatively, one of the location sensors 32 and 34 can comprise a bend sensor, which generates signals responsive to a bend radius of the spines 20. Such a bend sensor can comprise one or more piezoelectric sensors, as are known in the art, which generate electrical signals proportional to a force or torque exerted thereon when the catheter bends. Alternatively, a bend sensor can comprise one or more strain sensors, as are known in the art, or a fiberoptic sensor, wherein the bend radius is determined by measuring the loss and/or back-reflection of light in an optical fiber, as is also known in the art.

The coordinates of the distal sensor 32, relative to those of the proximal sensor 34, are determined and taken together with other known information pertaining to the curvature of the spines 20 of the basket-shaped mapping assembly 18. This information is used to find the positions of the ring electrodes 28 mounted on the spines 20.

Figure 3:
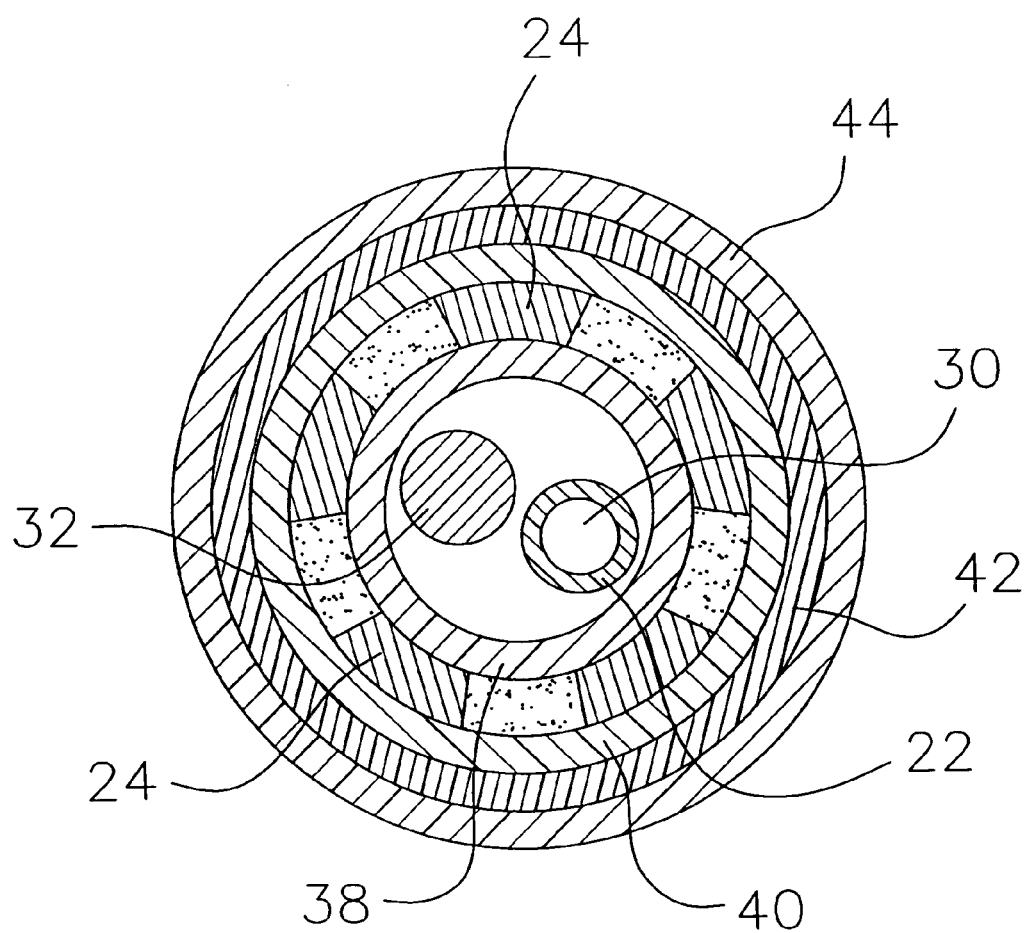
FIG. 3 is an end cross-sectional view of the distal end of the electrode assembly shown in FIG. 2.

A preferred construction of the distal end of the electrode assembly 18 is depicted in FIG. 3. The distal end of the expander 22 and the distal location sensor 32 are held together with a first short piece of plastic, preferably polyimide, tubing 38. The distal ends of the flexible Nitinol wires 24 that form the spines 20 are mounted, preferably evenly-spaced, around the first piece of tubing 38. The flexible wires 24 are held in place by a second short piece of plastic, preferably polyimide, tubing 40. A generally-rigid ring 42 is then mounted around the construction over the second short piece of tubing 40 to maintain a generally round shape. The generally-rigid ring 42 can be made of metal or plastic, so long as it is sufficient rigid to achieve the above-stated function. An outer tubing 44, preferably made of polyurethane or polyimide, then covers the entire construction over the generally-rigid ring 42 so that the distal end of the electrode assembly 18 is generally atraumatic. If desired, the construction can be held together by polyurethane glue or the like. The outer tubing 44 and generally-rigid ring 42 are slightly longer than the first and second plastic tubings 38 and 40, so that the proximal ends of the outer tubing and generally-rigid ring extend beyond the proximal ends of the first and second plastic tubings. The non-conductive coverings 26 extend into the outer tubing 44 and generally-rigid ring 42, but end before the first and second plastic tubings so that only the flexible wires 24 are mounted between the first and second plastic tubings. The sensor cable 36 attached to the distal location sensor 32 extends through one of the non-conductive coverings 26 and into the distal end of the catheter body 12, as described further below. As would be recognized by one skilled in the art, other arrangements for attaching the expander 22 to the distal ends of the flexible Nitinol wires 24 and for mounting the distal location sensor 32 near the distal end of the electrode assembly 18 could also be used in accordance with the invention.

Figure 4:
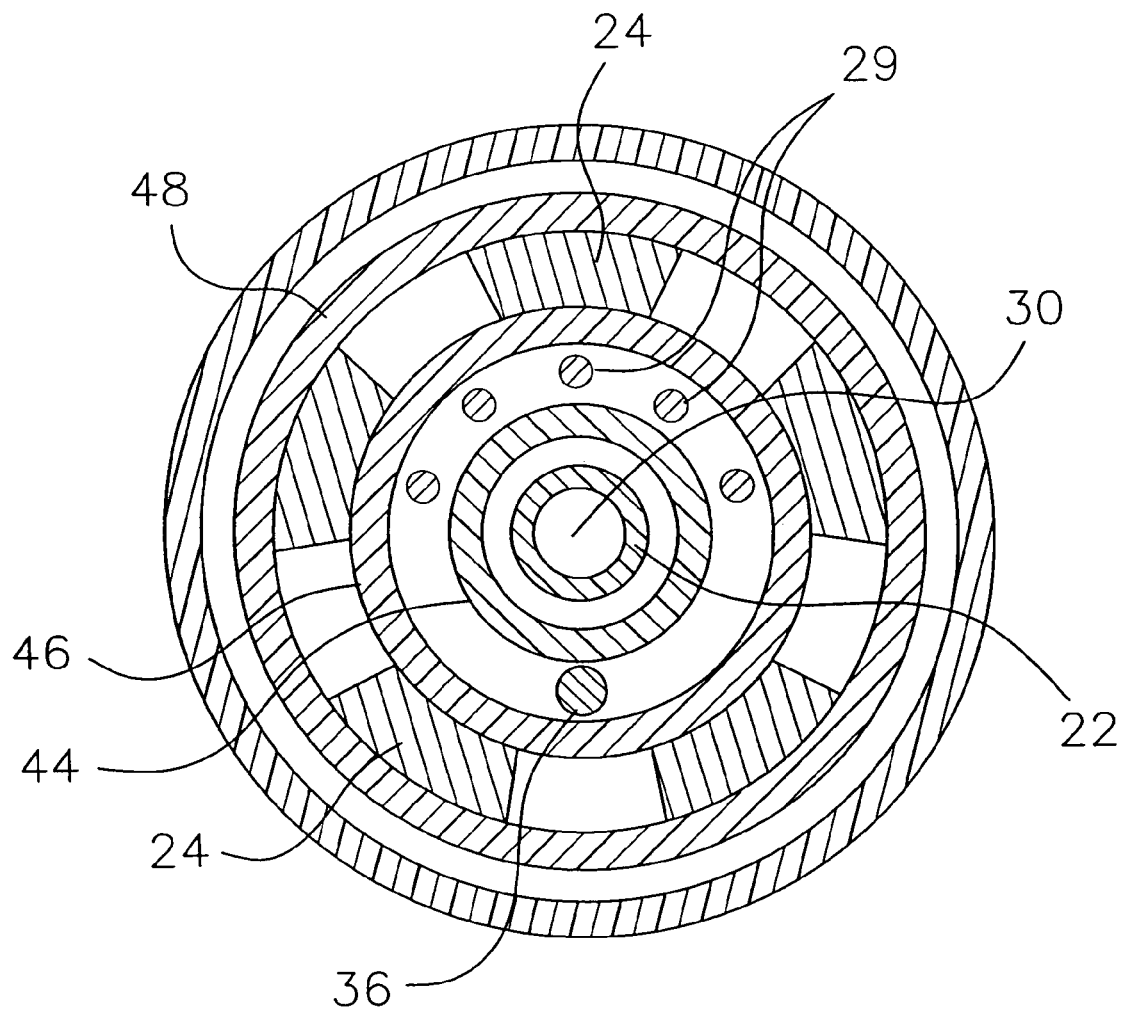
FIG. 4 is an end cross-sectional view of the housing and the distal end of the catheter body shown in FIG. 2.
Figure 5:
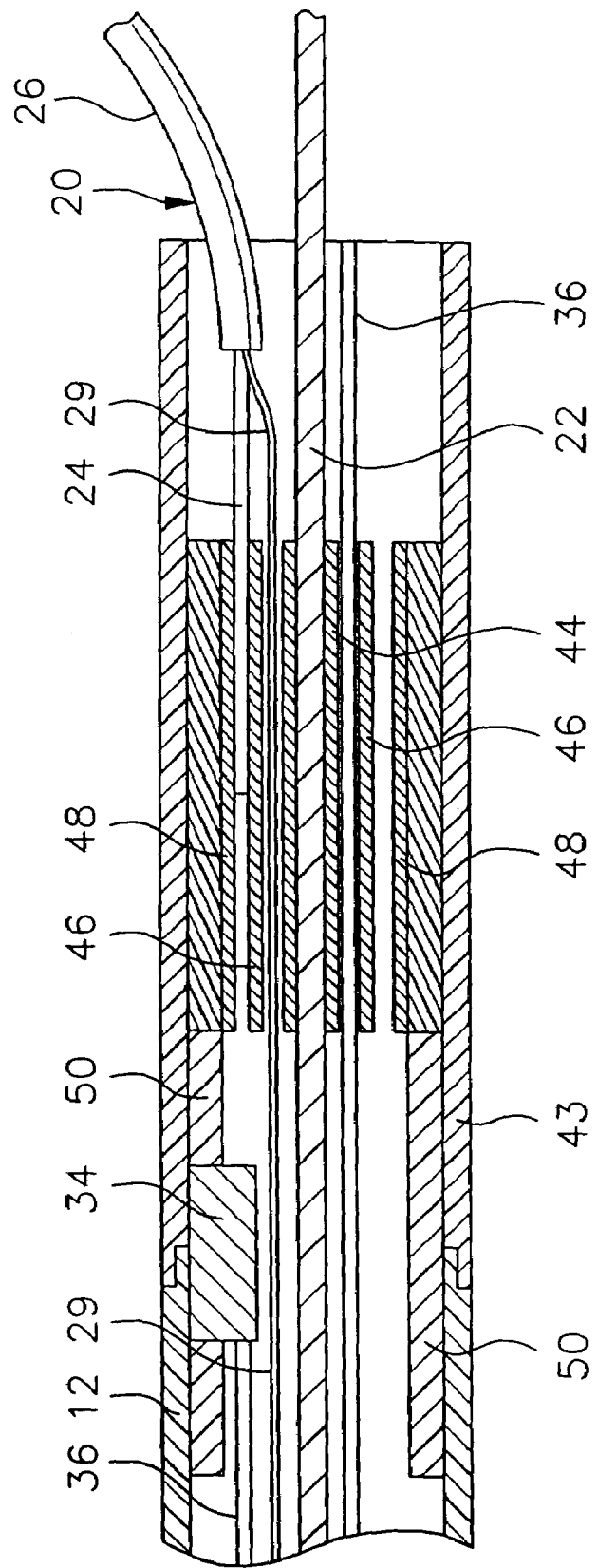
FIG. 5 is a side cross-sectional view of the housing and the distal end of the catheter body of the catheter shown in FIGS. 1 to 4.

A preferred construction of the proximal end of the electrode assembly 18 and distal end of the catheter body 12 is shown in FIGS. 4 and 5. In FIG. 5, only one spine 20 of the electrode assembly 18 is shown for clarity. A short plastic housing 43, preferably made of PEEK (polyether etherketone), joins the distal end of the catheter body 12 and proximal end of the electrode assembly 18 and houses the proximal location sensor 34. Preferably the plastic housing 43 has a length of about 11 mm. If the plastic housing 43 is too long, it can disadvantageously affect the flexibility of the distal end of the catheter body. The proximal end of the plastic housing 43 is mounted on the distal end of the catheter body 12 by any suitable method, preferably with polyurethane glue or the like.

The expander 22 must be afforded longitudinal movement within the catheter body 22. Accordingly, a tunnel 44 is formed from a piece of polyimide tubing or the like and is provided near the distal end of the catheter body 12 through which the expander 22 extends. The flexible Nitinol wires 24 are mounted, preferably evenly-spaced, between a proximal tubing 46 and an outer proximal ring 48, both of which are preferably made of polyimide, and held in place with polyurethane glue or the like. The proximal tubing 46 and outer proximal ring 48 are preferably relatively short, e.g., about 3 mm in length. Preferably the electrode lead wires 29 and sensor cable 36 that is attached to the distal location sensor 32 are also afforded some longitudinal movement within the catheter body 12 so that they do not break when the catheter body bends. Accordingly, in the depicted embodiment, the lead wires 29 and sensor cable 36 that is attached to the distal location sensor 32 extend within the proximal tubing 46 though which the expander 22 and tunnel 44 also extend, so that these components are not fixed in place along with the flexible Nitinol wires 24. This entire construction is mounted in the plastic housing 43. The proximal ends of the non-conductive coverings 26 of the spines 20 also extend into the plastic housing 43, but preferably end prior to the distal ends of the proximal tubing 46 and outer proximal ring 48.

The proximal location sensor 34 is also mounted within the housing 43. In the depicted embodiment, a second tunnel 50 is provided at the junction of the catheter body 12 and housing 43, with its proximal end extending into the catheter body and its distal end extending into the housing. The tunnel 50 is preferably made of polyimide and has a length ranging from about 5 to 7 mm. The tunnel 50 protects the expander 22, electrode lead wires 29 and sensor cable 36 that is attached to the distal location sensor 32 from being glued to the catheter at the junction of the catheter body and housing during assembly. Prior to assembly, the proximal location sensor 34 is mounted in a window 52 of the second tunnel 50. The proximal location sensor preferably has a length of about 1 to 3 mm. The sensor cable 36 attached to the proximal location sensor 34 extends through the second tunnel 50 and catheter body 12 along with the other components. Accordingly, all of these components are afforded longitudinal movement at the junction of the catheter body 12 and housing 43.

Figure 6:
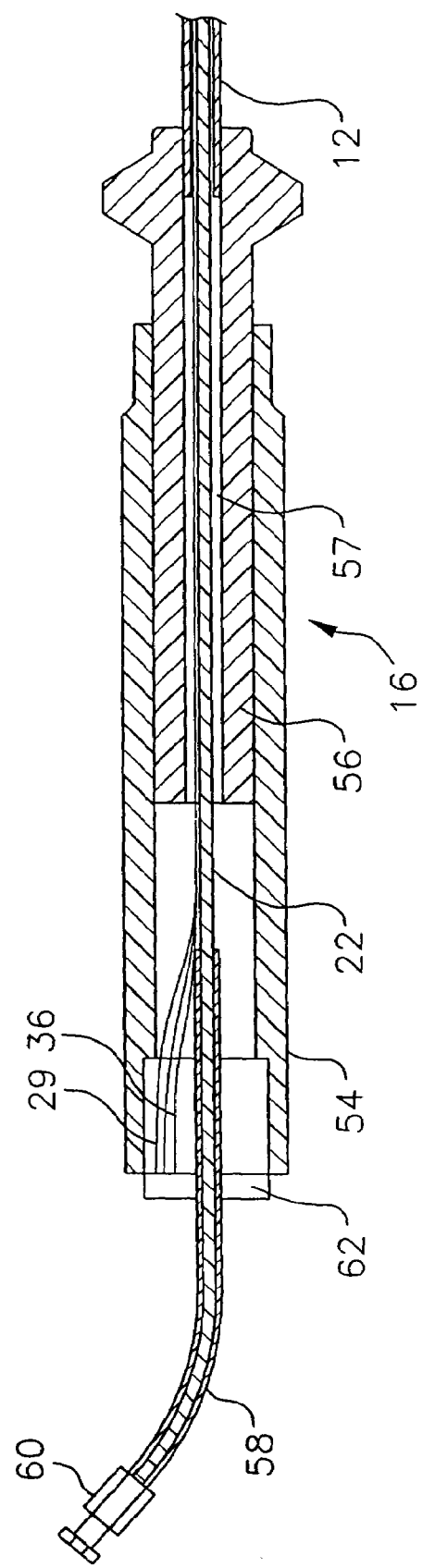
FIG. 6 is a side cross-sectional view of the control handle and the proximal end of the catheter body of the catheter shown in FIG. 1.

Longitudinal movement of the expander 22 relative to the catheter body 12, which results in expansion of the electrode assembly 18, is accomplished by manipulation of the control handle 16. As shown in FIG. 6, the control handle 16 comprises a generally-hollow handle housing 54 and a piston 56 slidably mounted within the distal end of the handle housing. The proximal end of the catheter body 12 is fixedly attached to the distal end of the piston 56 by a shrink sleeve (not shown), as is generally known in the art, or by any other suitable method.

Within the control handle 16, the proximal end of the expander 22 extends through a passage 57 in the piston 56, through the handle housing 54 and into a support tube 58, preferably made of braided polyimide or PEBAX.RTM. The support tube 58 extends out the proximal end of the control handle 16 and terminates in a luer hub 60. The support tube 58 and expander 22 are together fixedly attached to the handle housing 54 by any suitable method, preferably with polyurethane glue or the like. The guidewire lumen 30 of the expander 22 can also be used for infusion of fluids through the catheter, as is generally known in the art.

In a preferred embodiment, the piston 56 is approximately about 2 inches long, and the support tube 58 and expander 22 are attached to the handle housing 54 at a position about 0.5 inch distal to the proximal end of the handle and about 1 inch proximal to the proximal end of the piston in the neutral position. The piston is in the neutral position when the electrode assembly 18 is generally flat, i.e., not expanded.

The lead wires 29 and sensor cables 36 also extend through the piston passage 57 and handle housing 54 and are attached to a suitable connector 62 at the proximal end of the handle housing. Alternatively, the lead wires 29 and sensor cables 36 can extend through protective support tubes (not shown), similar to the support tube 58 that carries the expander 22, which have distal ends inside the handle housing 54 and proximal ends attached to appropriate connectors.

To use the catheter of the invention, an electrophysiologist introduces a guiding sheath, guidewire and dilator into the patient, as is generally known in the art. A suitable guiding sheath for use in connection with the inventive catheter is the PREFACE.TM. Braided Guiding Sheath (commercially available from Biosense Webster, Inc., Diamond Bar, Calif.). The dilator is removed, and the catheter is introduced through the guiding sheath whereby the guidewire lumen in the expander 22 permits the catheter to pass over the guidewire. The guiding sheath covers the spines 20 of the electrode assembly 18 internally in a collapsed position so that the entire catheter can be passed down a vein or artery to a desired location. Once the distal end of the catheter reaches the desired location, the guiding sheath is withdrawn. The expander 22 is then manipulated so that the spines 20 of the electrode assembly 18 flex outwardly into an expanded arrangement. In such an arrangement the spines 20 and the ring electrodes 28 contact the tissue of the heart. As will be recognized by one skilled in the art, the electrode assembly 18 can be fully or partially expanded in a variety of configurations depending on the configuration of the region of the heart being mapped.

Using the ring electrodes 28 on the spines 20 of the electrode assembly 18 in combination with the distal end proximal location sensors 32 and 34, the electrophysiologist can map local activation time, which can guide the electrophysiologist in providing therapy to the patient. The catheter can include one or more reference ring electrodes mounted on the catheter body 12, or one or more reference electrodes can be placed outside the body of the patient. By using the inventive catheter with the multiple electrodes 28 on the basket-shaped electrode assembly 18, the electrophysiologist can obtain a true anatomy of the heart by measuring less points than with traditional catheters, allowing him to map the heart more quickly. Moreover, by introducing the electrode assembly 18 over the guidewire, the electrophysiologist can remove the catheter from the heart and later reintroduce the electrode assembly to the same position after therapy, thereby permitting the electrophysiologist to accurately view the results of the therapy. Prior basket catheter designs did not permit this reproducibility.

If desired, the catheter can include a steering mechanism for deflection of the distal end of the catheter body 12. With such a design, the distal end of the catheter body 12 preferably comprises a short length of tubing, e.g., 2 to 4 inches, that is more flexible that the remainder of the catheter body. A suitable steering mechanism comprises a puller wire (not shown) that extends from a proximal end in the handle through the catheter body and into an off axis lumen in the catheter tip section. Within the catheter body, the puller wire extends through a closely wound coil that is bendable but substantially compressible. The coil is fixed near the proximal and distal ends of the catheter body and prevents deflection of the catheter body. The distal end of the puller wire is anchored at the distal end of the catheter body proximal to the proximal end of the basket. The proximal end of the puller wire is anchored to a movable member in the handle that can be moved relative to the catheter body. Proximal movement of the movable member relative to the catheter body results in deflection of the catheter tip section. An example of such a steering mechanism and construction is described in more detail in U.S. Pat. No. 6,064,905, the disclosure of which is incorporated herein by reference.

If a steering mechanism is included, the control handle 16 may be of any suitable construction for manipulating two wires, in this case, the expander 22 and a puller wire. Preferably the handle has a pair of movable members to which the expander and puller wire attach, such as handles typically used for bidirectional and multidirectional catheters. Examples of such handles are disclosed in U.S. Pat. Nos. 6,210,407, 6,198,974, 6,183,463, 6,183,435, 6,171,277, and 6,123,699, the disclosures of which are incorporated herein by reference.

In an alterative embodiment (not shown), the spines 20 do not include non-conductive coverings 26 so that the flexible Nitinol wires 24 each act as an elongated electrode. In such an embodiment, the sensor cable 36 attached to the distal location sensor 32 can extend through a second lumen (not shown) in the expander 22. Electrode lead wires 29 can then be attached to the proximal ends of the spines 20 within the catheter body 12. As would be recognized by one skilled in the art, other electrode configurations on the spines 20 could also be used in accordance with the invention.

In another alternative embodiment (not shown), the catheter does not include a control handle. In such an embodiment, the proximal end of the expander 22 will extend out the proximal end of the catheter body 12 and can be manipulated directly. However, such a design is less desirable from a practical standpoint, as it may be more difficult for the electrophysiologist to control.

The preceding description has been presented with references to presently preferred embodiments of the invention. Persons skilled in the art and technology to which this invention pertains will appreciate that alterations and changes in the described structures can be practiced without meaningfully departing from the principle, spirit and scope of this invention. Accordingly, the foregoing description should not be read as pertaining only to the precise structures described and shown in the accompanying drawings, but rather should be read as consistent with and as support for the following claims, which are to have their fullest and fairest scope.

What is claimed is:

1. A catheter comprising:
an elongated catheter body having proximal and distal ends and at least one lumen therethrough;
an electrode assembly at the distal end of the catheter body, the assembly having proximal and distal ends and comprising a plurality of spines, the spines comprising a plurality of electrodes;
an expander forming a longitudinal axis of the assembly, the spines attached at their distal ends to the expander, wherein the assembly has an expanded arrangement when the expander is moved proximally along the longitudinal axis relative to the catheter body and the assembly has a collapsed arrangement when the expander is moved distally along the longitudinal axis relative to the catheter body; and
a distal electrode location sensor mounted at or near the position where the distal ends of the spines are connected, and a proximal electrode location sensor mounted at or near the proximal end of the electrode assembly, whereby, in use, the coordinates of the distal electrode location sensor relative to those of the proximal electrode location sensor can be determined and taken together with known information pertaining to the curvature of the spines of the assembly to find the positions of each of the plurality of electrodes on the spines.

2. The catheter of claim 1, wherein the assembly is basket-shaped.

3. The catheter of claim 1, wherein the assembly is egg-shaped.

4. The catheter of claim 1, wherein the assembly is spherical.

5. The catheter of claim 1, wherein the spines bow radially outward when the assembly is in the expanded arrangement.

6. The catheter of claim 1, wherein each spine has a non-conductive outer surface on which one or more ring electrodes are mounted.

7. The catheter of claim 1, wherein each spine comprises an internal flexible wire and a non-conductive covering over the flexible wire on which one or more ring electrodes are mounted.

8. The catheter of claim 7, wherein the internal flexible wire of each spine comprises nitinol.

9. The catheter of claim 1, wherein the electrode assembly has at least three spines.

10. The catheter of claim 1, wherein the electrode assembly has at least five spines.

11. The catheter of claim 1, wherein the proximal electrode location sensor is mounted in the distal end of the catheter body.

12. The catheter of claim 1, wherein the proximal and distal electrode location sensors each comprise an electromagnetic location sensor.

13. The catheter of claim 1, wherein the expander has a proximal end attached to a control handle.

14. The catheter of claim 1, wherein the expander comprises a puller wire.

15. The catheter of claim 1, wherein the expander has a lumen extending therethrough.

16. The catheter of claim 1, further comprising at least one ring electrode mounted on each spine.

17. The catheter of claim 1, wherein each of the distal and proximal location sensors comprises at least one magnetic-field-responsive coil.

18. The catheter of claim 17, wherein each location sensor comprises six magnetic-field-responsive coils.

19. The catheter of claim 18, wherein the expander comprises plastic tubing.

20. The catheter of claim 18, wherein the expander comprises braided plastic tubing.

21. The catheter of claim 18, wherein the expander comprises braided polyimide tubing.

22. The catheter of claim 1, wherein each of the distal and proximal location sensors comprises a bend sensor, wherein the bend sensor is adapted to generate signals responsive to a bend radius of the spines.

23. The catheter of claim 22, wherein each bend sensor comprises a piezoelectric sensor, wherein the piezoelectric sensor is adapted to generate electrical signals proportional to a force or torque exerted on the sensor when the catheter bends.

24. A catheter comprising:
an elongated catheter body having proximal and distal ends and at least one lumen therethrough;
a basket-shaped electrode assembly at the distal end of the catheter body, the basket-shaped electrode assembly having proximal and distal ends and comprising a plurality of spines, the spines comprising a plurality of electrodes,
an expander configured to expand and contract the basket-shaped electrode assembly with longitudinal movement relative to the catheter body, the spines being connected at their distal ends to the expander, and,
a distal electrode location sensor mounted at or near the position where the distal ends of the spines are connected, and a proximal electrode location sensor mounted at or near the proximal end of the electrode assembly, whereby, in use, the coordinates of the distal electrode location sensor relative to those of the proximal electrode location sensor can be determined and taken together with known information pertaining to the curvature of the spines of the assembly to find the positions of each of the plurality of electrodes on the spines.

25. The catheter of claim 24, wherein the expander is configured with a guidewire lumen extending therethrough.

26. The catheter of claim 24, wherein each of the distal and proximal location sensors comprises an electromagnetic location sensor.

27. The catheter of claim 24, further comprising at least one ring electrode on each spine.

28. The catheter of claim 24, wherein each of he distal and proximal location sensors comprises at least one magnetic-field-responsive coil.

29. The catheter of claim 28, wherein each location sensor comprises six magnetic-field responsive coils.

30. The catheter of claim 24, wherein each of the distal and proximal location sensors comprises a bend sensor, wherein the bend sensor is adapted to generate signals responsive to a bend radius of the spines.

31. The catheter of claim 30, wherein each bend sensor comprises a piezoelectric sensor, wherein the piezoelectric sensor is adapted to generate electrical signals proportional to a force or torque exerted on the sensor when the catheter bends.

* * * * *